(12) United States Patent
Cotton et al.

(10) Patent No.: US 7,916,910 B2
(45) Date of Patent: Mar. 29, 2011

(54) IMAGE PROCESSING METHOD AND APPARATUS

(75) Inventors: Symon D'Oyly Cotton, Great Gransden (GB); Robert James Morse, Cambridge (GB); Mark Chellingworth, Llandough (GB); Stephen John Preece, Cheadle Hulme (GB)

(73) Assignee: Biocompatibles UK Limited, Surrey (GB)

( * ) Notice: Subject to any disclaimer, the term of this patent is extended or adjusted under 35 U.S.C. 154(b) by 1037 days.

(21) Appl. No.: 11/524,803

(22) Filed: Sep. 21, 2006

(65) Prior Publication Data

US 2008/0075340 A1  Mar. 27, 2008

(30) Foreign Application Priority Data

Sep. 23, 2005  (GB) .................................. 0519497.2

(51) Int. Cl.
*G06K 9/00*  (2006.01)
*A61B 6/00*  (2006.01)

(52) U.S. Cl. ......................................... 382/128; 600/475

(58) Field of Classification Search .......... 382/128–132; 600/475

See application file for complete search history.

(56) References Cited

U.S. PATENT DOCUMENTS

| | | | |
|---|---|---|---|
| 5,701,902 A * | 12/1997 | Vari et al. ........................ | 600/473 |
| 6,324,417 B1 | 11/2001 | Cotton et al. | |
| 6,418,238 B1 * | 7/2002 | Shiratani et al. ............... | 382/133 |
| 6,571,003 B1 * | 5/2003 | Hillebrand et al. ............ | 382/118 |
| 7,054,674 B2 | 5/2006 | Cane et al. | |
| 7,132,943 B2 | 11/2006 | Nelson | |
| 7,400,754 B2 * | 7/2008 | Jung et al. ...................... | 382/128 |
| 2001/0056237 A1 * | 12/2001 | Cane et al. ...................... | 600/475 |
| 2003/0139672 A1 | 7/2003 | Cane et al. | |
| 2004/0066959 A1 * | 4/2004 | Pike et al. ....................... | 382/128 |
| 2004/0085324 A1 | 5/2004 | Yao | |
| 2005/0030372 A1 | 2/2005 | Jung et al. | |
| 2006/0089553 A1 | 4/2006 | Cotton et al. | |

FOREIGN PATENT DOCUMENTS

| | | |
|---|---|---|
| GB | 236007 | 7/1925 |
| GB | 2396007 | 6/2004 |
| WO | WO 00/76398 A1 | 12/2000 |
| WO | WO 02/02001 A3 | 1/2002 |
| WO | WO 02/37421 A1 | 5/2002 |

OTHER PUBLICATIONS

Tsumura et al, "Independent-Component Analysis of Skin Color Image", J. Opt. Soc. Am. A., vol. 16 No. 9, 2169-2176 (1999).
Tsumura et al, "Mapping Pigmentation in Human Skin from Multi-Channel Visible Spectrum Image by Inverse Optical Scattering Techique", J. of Imaging Science and Tech., vol. 45 No. 5, 444-450 (2001).

(Continued)

*Primary Examiner* — Vu Le
*Assistant Examiner* — Amara Abdi
(74) *Attorney, Agent, or Firm* — Oliff & Berridge, PLC

(57) ABSTRACT

An image of an individual (2) is obtained via a digital camera (1). The RGB image data is then processed to derive from the image data data representative of the distribution of chromophores resulting in the appearance of the individual (2). A calculated chromophore distribution is then utilised to derive a revised chromophore distribution representing the effect of the desired cosmetic or surgical intervention or medical condition. This chromophore distribution is then processed to generate an output image (34) illustrating the expected result of that intervention. The generated image (34) can be displayed simultaneously with an original image (33) so that the extent of expected improvement can be determined.

23 Claims, 11 Drawing Sheets

OTHER PUBLICATIONS

Uetsuki et al, "Correlation Map Analysis Between Appearance of Japanese Facial Images and Amount of Melanin and Hemoglobin Components in the Skin", Proc. SPIE 4299, 252-260 (2001).

Tsumura et al, "Image-Based Skin Color and Texture Analysis/Synthesis by Extracting Hemoglobin and Melanin Information in the Skin", acm Transactions on Graphics, vol. 22 No. 3, 770-779 (2003) (Proceedings of ACM Siggraph 2003).

Tsumura, Norimichi et al., "*Image-based skin color and texture analysis/synthesis by extracting hemoglobin and melanin information in the skin*," ACM Transactions of Graphics, Jul. 2003, vol. 22, pp. 770-779, ACM.

Heeger, David J. et al., "*Pyramid-Based Texture Analysis/Synthesis*," Proceedings of the International Conference on Image Processing (ICIP), Oct. 1995, vol. 3, pp. 648-651, IEEE, U.S.

European Patent Office, *European Search Report for Patent Application No. EP 06 45 4907*, dated Sep. 30, 2008, pp. 1-12.

\* cited by examiner

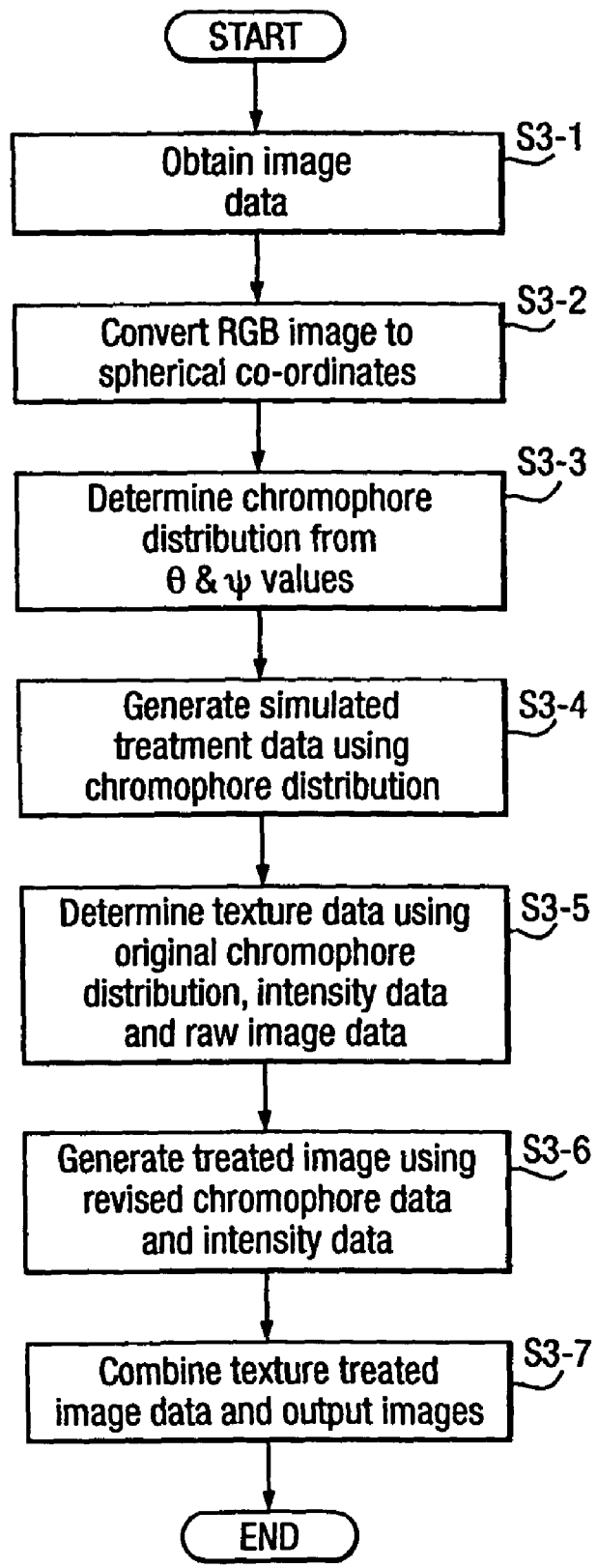

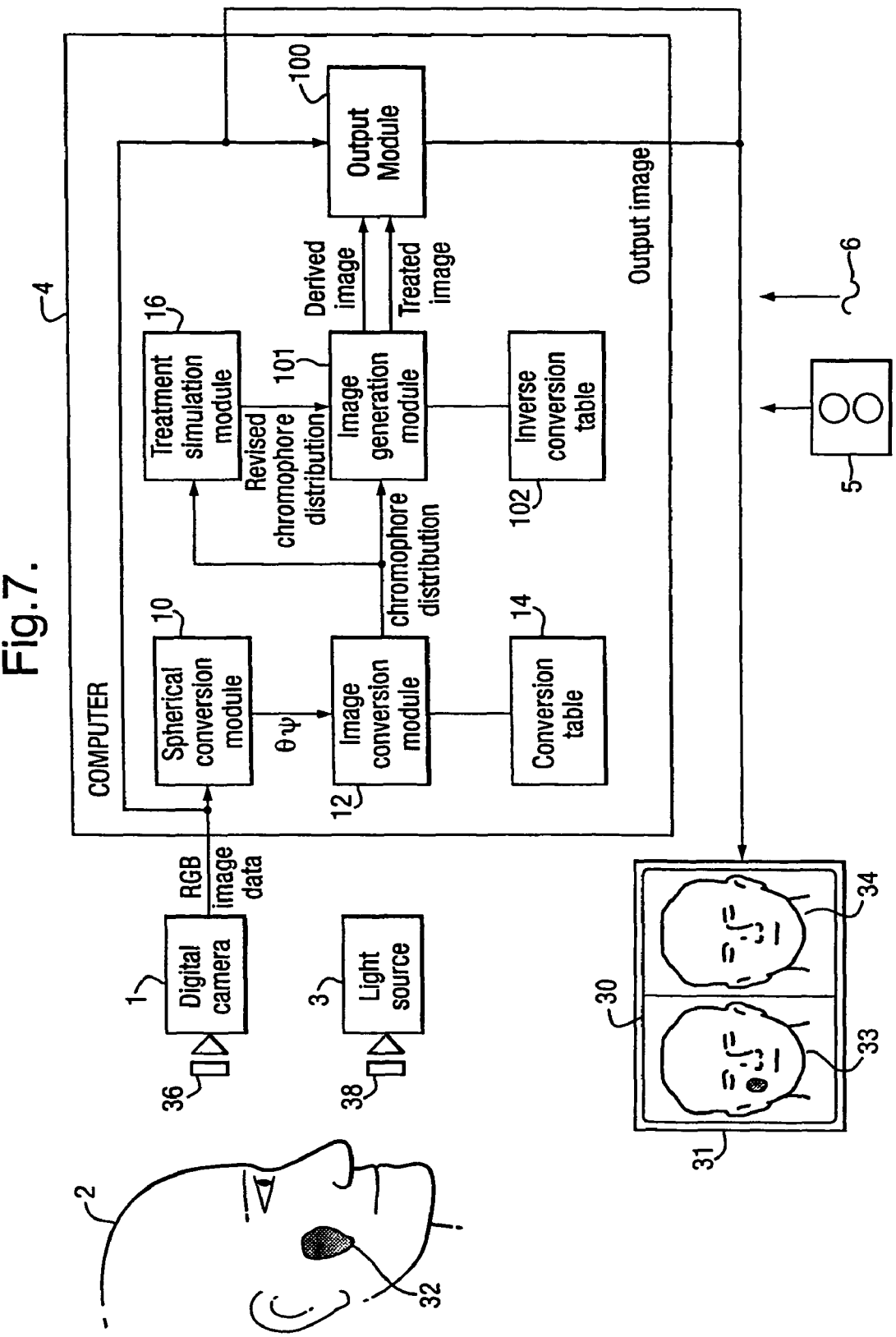

IMAGE PROCESSING METHOD AND APPARATUS

CROSS-REFERENCE TO RELATED APPLICATION

This application claims the benefit of United Kingdom Patent Application No. 0519497.2 filed Sep. 23, 2005. The entire disclosure of United Kingdom Patent Application No. 0519497.2 is hereby incorporated herein by reference.

FIELD OF THE INVENTION

Embodiments of the present invention generally relate to image processing. In particular embodiments of the present application concern methods and apparatus for processing images of individuals to generate images representative of the results of cosmetic or surgical interventions or the progression of medical conditions.

BACKGROUND OF THE INVENTION

Many skin conditions for example thread veins and age spots can adversely affect the appearance of individuals. Various cosmetic and surgical techniques have therefore been developed to address these conditions. Thus for example the appearance of thread veins can be minimised through laser cauterisation of the affected blood vessels. Similarly the appearance of age spots can be addressed through the application of an acid peel.

In order to determine whether a particular intervention is worth pursuing, it is useful for an individual to be given an indication of the likely results of the intervention prior to undertaking a course of treatment. It is desirable that such representations are as accurate as possible. There is therefore a need for image processing methods and apparatus which enable such images to be generated in such a way that they can be more accurate representations of the likely results of an intervention than exists in the prior art.

SUMMARY OF THE INVENTION

In accordance with one aspect of the present invention there is provided a method of generating an image of an individual comprising: storing model data defining a model of the variations in appearance of skin arising due to different concentrations of at least one chromophores; obtaining an image of an individual; processing the image utilising said stored model data to determine the distribution of at least one chromophore responsible for the appearance of the individual in the image; determining a revised distribution of said at least one chromophore; and generating a representation of said individual in said image utilising said determined revised distribution of said at least one chromophore and said stored model data.

In accordance with an embodiment of the present invention, the generation of a representation of an individual in an image may comprise: utilising a determined distribution of at least one chromophore in the skin of an individual in an image to determine variations in appearance of said individual arising from factors other than the distribution of said at least one chromophores; and generating a representation of said individual in said image utilising said determined revised distribution of said at least one chromophore, said stored model data and said determined variations in appearance of said individual determined not to arise from the distribution of said at least one chromophore.

BRIEF DESCRIPTION OF THE DRAWINGS

Embodiments of the present invention will be more readily understood from the detailed description of exemplary embodiments presented below considered in conjunction with the attached drawings, of which:

FIG. 3 is a flow diagram of the processing performed by the image processing system of FIG. 1;

accompanying drawings in which:

FIG. 7 is a schematic block diagram of an image processing system in accordance with a second embodiment of the present invention;

While the invention is described herein by way of example using several embodiments and illustrative drawings, those skilled in the art will recognize the invention is not limited to the embodiments of the drawings described. It should be understood the drawings and detailed description thereto are not intended to limit the invention to the particular form disclosed, but to the contrary, the invention is to cover all modification, equivalents and alternatives. Thus, it is to be understood that the attached drawings are for purposes of illustrating the concepts of the invention and may not be to scale.

DETAILED DESCRIPTION

First Embodiment

Figure 1:
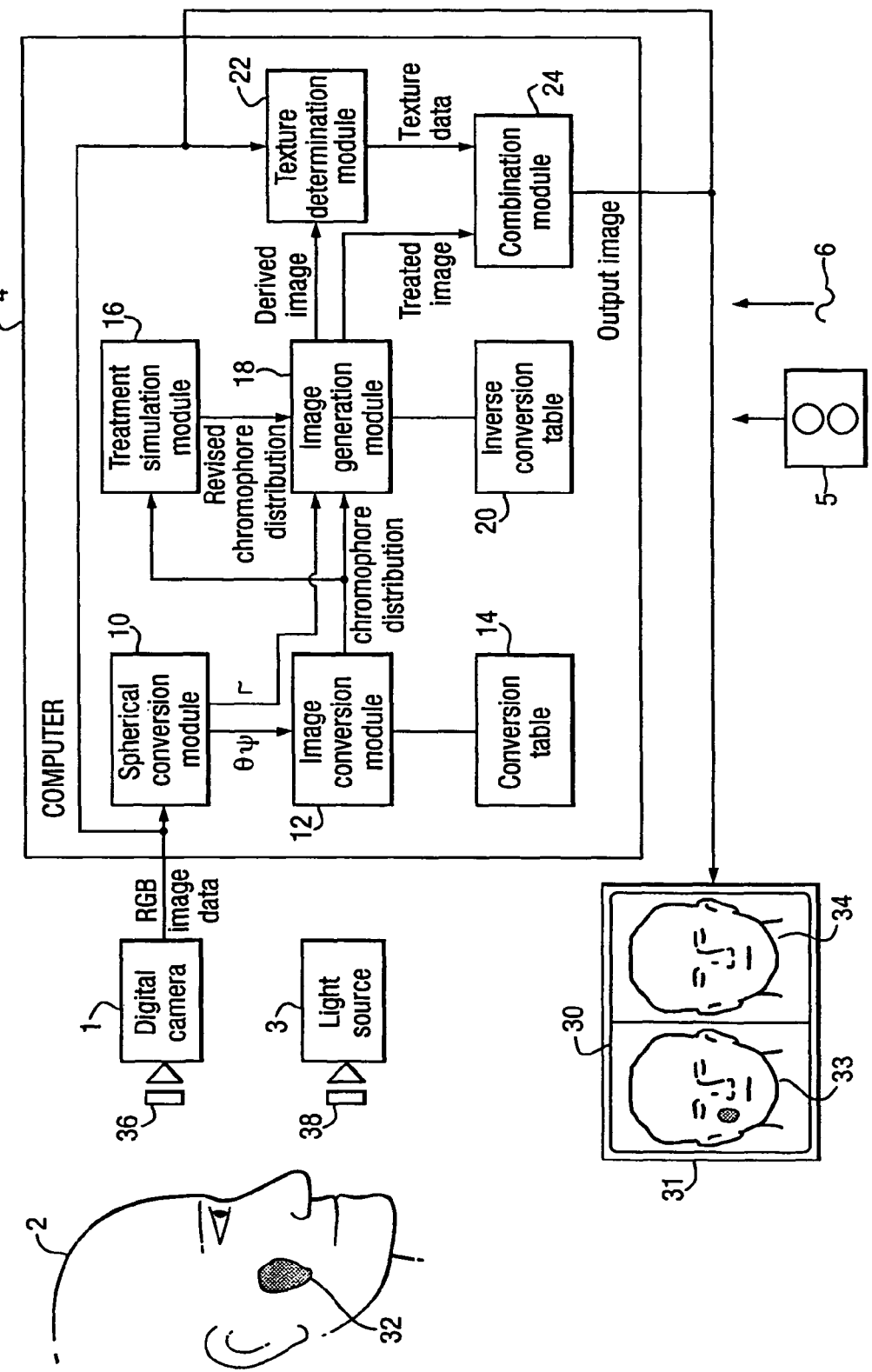
FIG. 1 is a schematic block diagram of an image processing system in accordance with a first embodiment of the present invention.

FIG. 1 is a schematic block diagram of a first embodiment of the present invention. In accordance with this embodiment, a digital camera 1 comprising a conventional digital camera is provided which is arranged to obtain an image of an individual 2 illuminated by a light source 3. The images obtained by the digital camera 1 are then transmitted to a computer 4 which is configured by software either provided on a disk 5 or by receiving an electrical signal 6 by via a communications network to be configured into a number of functional modules 16-24 which cause the computer 4 to process the image data received from the digital camera 1 to generate an output image 30 which is shown on a display 31.

In this embodiment where the individual is shown with a cosmetic disfigurement 32 on their cheek the output image 30 comprises a first image portion 33 being a representation of the original image data generated by the digital camera 1 and a second image portion 34 being a calculated representation of the individual 2 illustrating the expected results from a treatment affecting the individual 2.

Interaction of Light with the Skin

Prior to describing the detailed processing of the various functional modules 10-24 of the computer 4, the physical structure of skin and the interaction of skin with light will be briefly explained with reference to FIG. 2.

Figure 2:
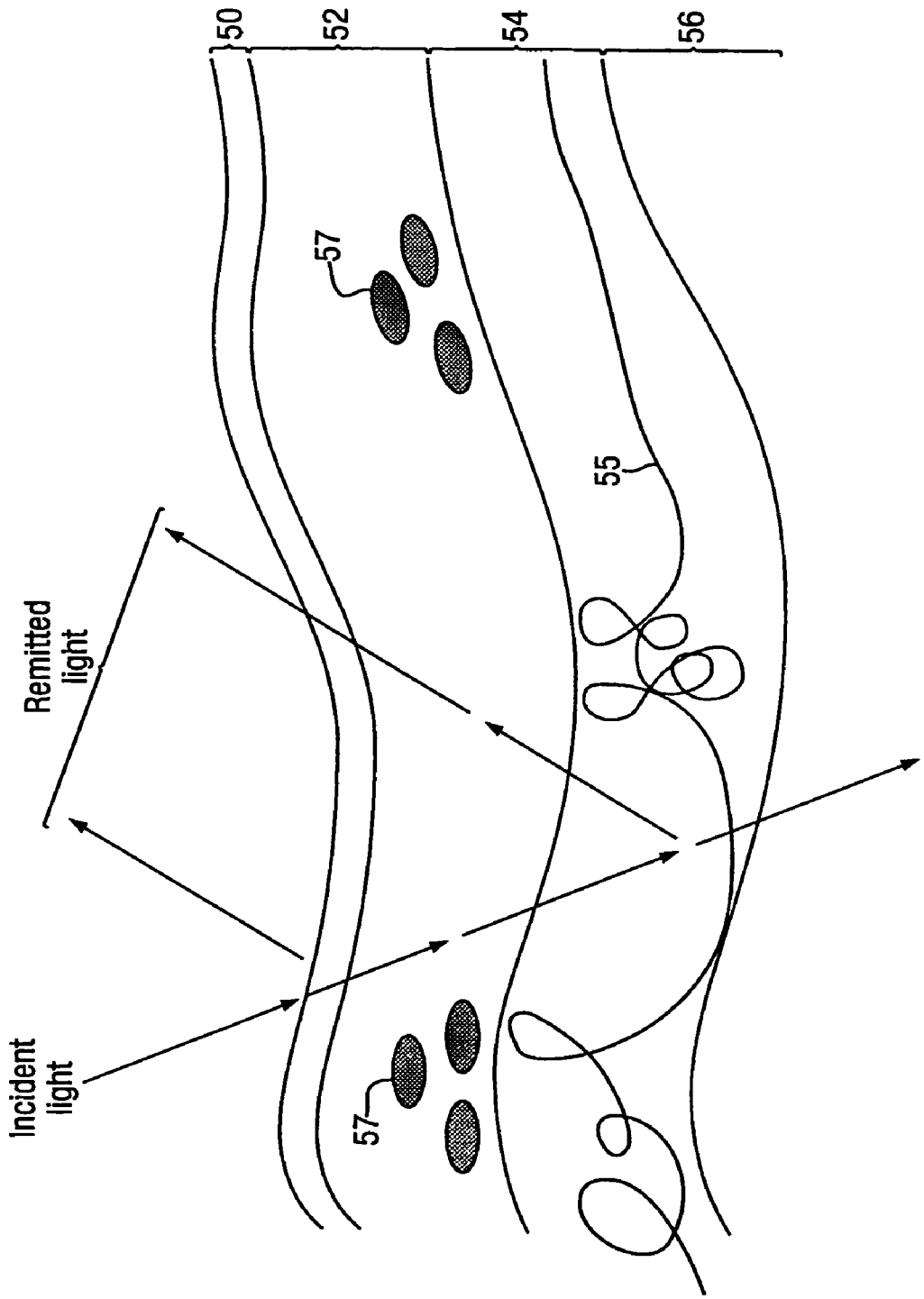
FIG. 2 is a schematic cross sectional view through a layer of skin illustrating the structure of the skin and the interaction of that structure with incident light.

As shown in FIG. 2, skin has a layered structure comprising an outer cornified layer 50, the epidermis 52, and the dermis which itself can be divided into the papillary dermis 54 which contains the blood supply 55 for the skin and the reticular dermis 56.

When light is incident on the skin, much of the light is immediately reflected when coming into contact with the outer cornified layer 50. A proportion of incident light does, however, pass through the cornified layer 50 and proceeds to interact with the constituents of the epidermis 52 and the papillary dermis 54. As light passes through the epidermis 52 and the papillary dermis 54 the light is absorbed by various chromophores present in the skin, most notably chromophores such as haemoglobin present in the blood in blood vessels 55 in the papillary dermis, melanin, a pigment produced by melanocytes 57 in the epidermis 52 and collagen a fibrous material present throughout the skin. By the time the incident light reaches the reticular dermis 56 the scattering of light is highly forward and therefore for that reason the reticular dermis 56 can for all intents and purposes be considered returning no light.

In addition to chromophores present in the epidermis 52 and papillary dermis 54 absorbing various wavelengths, certain structures in the skin most notably collagen cause incident light to be reflected. The outward appearance of the skin can therefore be considered to be a mixture of the light immediately reflected by the cornified layer 50 and the remitted light which has interacted with the chromophores present in the epidermis 52 and the papillary dermis 54. As has been demonstrated in the applicant's prior U.S. Pat. No. 6,324,417 and co-pending U.S. patent application Ser. No. 09/760,387, U.S. patent application Ser. No. 10/240,071, U.S. patent application Ser. No. 10/521,639 and U.S. patent application Ser. No. 10/532,158 all of which are hereby incorporated by reference it is possible to process light remitted from the skin to obtain measurements of various chromophores present in the skin.

In order to obtain measurements of the concentrations and distribution of chromophores in the papillary dermis 54 and epidermis 52, the effect of reflection of light directly by the cornified layer 50 is required to be removed so that a measurement of the remitted light which has interacted with the chromophores present in the epidermis 52 and papillary dermis 54 can be made.

Returning to FIG. 1, in this embodiment a first polarising filter 36 is provided in front of the lens of the digital camera 1 and a second polarising filter 38 cross polarised with the first is provided in front of the light source 3. As the interaction of light with collagen in the skin is such to cause the light to lose its polarisation, by providing these filters. Light from the light source 3 passing through the second polarising filter 38 which is reflected directly by the cornified layer 50 without interacting with the other layers of the skin is caused to be filtered by the first polarising filter 36. The image data obtained by the digital camera 1 is thereby caused to be solely representative of the light remitted which has interacted with the structures of the epidermis 52 and papillary dermis 54 of an individual's skin.

As stated previously, software provided on a disk 5 or as an electrical signal 6 via a communications network causes the memory and processors of the computer 4 become configured as a number of functional modules.

The functional modules illustrated in FIG. 1 are purely notional in order to assist with the understanding of the working of the claimed invention and may not in certain embodiments directly correspond with blocks of code in the source code for the software. In other embodiments the function performed by the illustrated functional modules may be divided between different modules or may be performed by the re use of the same modules for different functions.

In the present embodiment the functional modules comprise a spherical conversion unit 10 for converting RGB image data into corresponding spherical co-ordinates, an image conversion module 12 and a conversion table 14 for processing spherical angular co-ordinates to generate data indicative of concentrations of blood and melanin; a treatment simulation module 16 arranged to determine a revised chromophore distribution representative of a treatment by processing chromophore distributions generated by the conversion module 12; an image generation module 18 and an inverse conversion table 20 operable to generate image data utilising chromophores distribution data; a texture determination module 22 for identifying variations in appearance in an image of an individual which do not arise due to variations in chromophore concentrations; and a combination module 24 for combining texture data generated by the texture determination module 22 and image data generated by the image generation module 18 and outputting a simulated treated image 34 for display on a display screen 31.

Processing of Obtained Image Data

Referring to FIG. 3 which is a flow diagram of the processing performed by the computer 4 of FIG. 1, initially (S3-1) an image is obtained by the digital camera 1 of the individual 2 illuminated by the light source 3. In this embodiment the digital camera 1 comprises a conventional digital camera. The image data generated by the digital camera 1 therefore comprises RGB values ranging from 0 to 255 for a large array of pixels where the RGB values are indicative of the extent light received by a photo receptor within the camera 1 for each pixel in an image appears to be red, green and blue where a completely black pixel has RGB values of 0, 0, 0 and a completely bright white pixel has RGB values of 255, 255, 255.

When an image of an individual 2 has been obtained by the camera 1, the image is initially passed to the spherical conversion module 10 which converts (S3-2) the conventional RGB data for each pixel in an image into a corresponding set of spherical co-ordinates θ ψ r where the spherical angles of θ ψ are substantially indicative of the hue and chromaticity represented by an individual pixel in an image captured by the digital camera 1 and the radial co-ordinate r is substantially indicative of the brightness of the pixel.

This conversion is achieved in a conventional manner with $\theta = \cos^{-1}(B(R^2+B^2G^2)^{-1/2})$ $\psi = \tan^{-1}(G/R)$ and $r = (R^2+B^2+G^2)^{1/2}$ The conversion is performed for each pixel in the original pixel array for the image generated by the digital camera. The result of the conversion is a set of spherical θ ψ r co-ordinates for each pixel in the original image.

The array of radial elements r is then passed directly to the image generation module 18 whereas arrays of the calculated angular spherical co-ordinates θ and ψ are in this embodiment passed to the image conversion module 12.

After the spherical conversion module 10 has converted the RGB values for an image into spherical co-ordinates, the image conversion module 12 then processes the generated array of θ and ψ values to obtain values indicative of the concentration of blood and melanin at individual points on the surface of the skin of the individual.

In this embodiment this is achieved by processing each pair of θ and ψ values for each pixel in an array in turn by scaling the θ and ψ values so that instead of comprising values between π and −π, and 0 and π/2, the scaled θ and ψ values comprise integer values ranging between 0 and 255. These scaled θ and ψ values are then utilised to access the conversion table 14 which in this embodiment is a 255 by 255 a lookup table associating pairs of scaled θ and ψ co-ordinates with pairs of concentrations of blood and melanin liable to give rise to such scaled θ and ψ values. In this embodiment, the conversion table 14 comprises a table associating blood and melanin concentrations with various θ and ψ values, where the θ and ψ values fall within the expected range of the colour space for skin. In the event that the combination of θ and ψ values for a particular pixel falls outside the range of values for which chromophores concentration data is stored within the conversion table 14, in this embodiment the conversion module 12 returns a null value for the concentration of blood and melanin for the pixel with θ and ψ values for the pixel.

Figure 4A:
FIG. 4A is an exemplary original image of an individual.
Figure 4B:
FIG. 4B is an image representative of a determined distribution of blood derived for the image of FIG. 4A.
Figure 4C:
FIG. 4C is an image illustrating a determined distribution of melanin of the image of FIG. 4A.

By way of example referring to FIGS. 4A, B and C, FIG. 4A is an illustrative example of an image of an individual's face captured by a digital camera 1. The pixels in the image will each comprise a red, green and blue pixel value. FIGS. 4B and 4C are illustrative representations of determined concentrations of blood and melanin respectively derived by processing the exemplary image of FIG. 4A where greater concentrations of blood and melanin are shown by darker points within the images.

The applicants have appreciated through analysis of the remittance of light from the skin that under controlled lighting using polarised white light, light remitted by the skin lies within a well defined colour space. In this colour space apparent hue or colour of a portion of skin is predominantly accounted for through variations in blood and melanin concentration. Conversely, the brightness of a particular portion of skin is primarily determined through a combination of: the brightness of light incident on the skin, the angle at which light illuminates a particular portion of skin, the distance between a subject and a light source, and the concentration of collagen at a particular point since the concentration of collagen makes skin more or less reflective.

Through this analysis, the applicants have further appreciated that under uncontrolled illumination conditions where the strength, distance and angle of illumination of light is not controlled, variations in strength, distance and angle of illumination cause significant variations in the apparent brightness of the skin but have only a limited effect on the apparent colour or hue of the skin. Thus when the RGB values for a pixel in a digital image obtained by a digital camera 1 are converted to spherical co-ordinates, the variation in brightness due to variation in illumination and collagen concentration is primarily accounted for through variations in the radial r value for a particular image pixel. In contrast, the angular values θ ψ obtained through converting an RGB image to spherical co-ordinates are primarily determined by variations in concentration of blood and melanin and such values are substantially independent of lighting geometry. The applicants have therefore appreciated that measurements of the concentrations of blood and melanin can be determined by processing solely the angular values alone thereby reducing the amount of data required to derive measurements of such concentrations from an image captured by the camera 1.

Returning to FIG. 3, after chromophore distribution values for blood and melanin for each of the pixels in an image have been calculated by the conversion module 12, this chromophore distribution data is then passed by the conversion module 12 to the treatment simulation module 16 and the image generation module 18. When the chromophore distribution values are received by the treatment simulation modules 16, the treatment simulation module 16 then (S3-4) processes the received chromophore distribution data to generate revised chromophore distribution data indicative of the chromophore distribution after a treatment.

By way of example in the case of the individual appearing in the image of FIG. 4A, the individual has a number of thread veins on their cheek shown in the left hand side of the image of FIG. 4A. These thread veins may more clearly be observed in the enlarged image of FIG. 5A and in corresponding enlarged image portion of FIG. 4B shown as FIG. 5B.

Such thread veins arise due to excessively large blood vessels being present near the surface of the skin. These thread veins can be treated through cauterisation of the unwanted blood vessels. In order to illustrate to an individual the result of such intervention, in this embodiment the treatment simulation module 16 processes the received chromophore distribution data representing the concentration of blood to generate revised blood distribution data which is the expected distribution of blood after treatment.

In this embodiment which is an illustrative example of processing an image to remove the appearance of thread veins, the revised blood distribution data is determined through applying a conventional blurring algorithm to the portions of the image where treatment would occur.

Figure 4D:
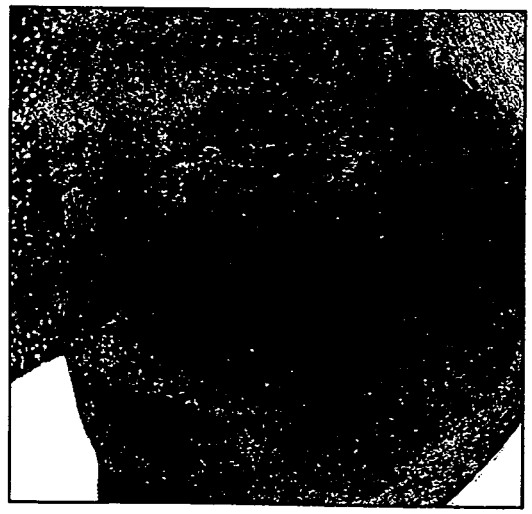
FIG. 4D is an image illustrating a revised distribution of blood determined by processing the image of FIG. 4B.

The result of processing the image of FIG. 4B using such a blurring algorithm is shown as FIG. 4D. The result of processing these specific areas of image highlighted in FIG. 5B is shown as FIG. 5C. As can be seen by comparing FIGS. 4B and 4D and FIGS. 5B and 5C, the result of processing by the treatment simulation module 16 in this embodiment is to generate blood distribution data illustrating a distribution of blood where the blood is more smoothly distributed than exists in the original calculated distribution for the individual.

Returning to FIG. 3, in addition to passing chromophore distribution data to the treatment simulation model 16, the conversion model 12 also passes the chromophore distribution data to the image generation module 18 which together with the inverse conversion table 20 and the texture determination module 22 proceeds to determine (S3-5) texture data indicative of the variation in appearance of an individual which does not arise due to different distributions of chromophores.

More specifically as has previously been explained, the majority of the variation in apparent brightness of portions of an individual's skin arises due to variations in collagen concentration and in illumination whereas the apparent hue of portions of an individual's skin largely arises due to variations in the distribution and concentration of chromophores principally blood and melanin. Other factors do however affect the appearance of an individual. Typically such factors include variations arising due to the small scale texture of the skin. It is, however, possible to identify these variations in appearance which arise due to other factors as will now be explained.

In this embodiment initially the image generation module 18 processes the unamended chromophore distribution data for each pixel in an image to generate a corresponding expected pair of $\theta$ and $\psi$ colour angles. In this embodiment this conversion is achieved by the image generation module 18 accessing the inverse conversion table 20 which is a lookup table which associates each possible pair of determined blood and melanin concentrations for a pixel with a corresponding expected $\theta$ and $\psi$ values. The inverse conversion table 20 is therefore data representative of an inverse function corresponding to the function for converting $\theta$ and $\psi$ values to measurements of blood and melanin concentration as is stored in the conversion table 14. In the case of pixels which are associated with null values of within the chromophore distribution data no $\theta$ and $\psi$ values are determined.

By processing the chromophore distribution data in this way, and accessing the radial co-ordinates r for pixels generated by the spherical conversion module 10, the image generation module 18 is able to generate a derived image where each pixel image for which the conversion module 12 is able to determine chromophore distribution values is represented by a pair of calculated colour angles $\theta$ and $\psi$ and a radial value r corresponding to the radial value for that particular pixel as determined by the spherical conversion module 10.

This derived image data is then passed to the texture determination module 22 which proceeds to convert the array of received $\theta$ $\psi$ r data into an image of equivalent RGB values.

This is achieved by applying the following equations to the $\theta$ $\psi$ r data for each pixel:

$R = r \sin \theta \cos \psi$ $G = r \sin \theta \sin \psi$ $B = r \cos \theta$

The texture determination module 22 then performs a difference operation comparing for each pixel the calculated RGB values for that pixel with the corresponding RGB values in the original image data obtained by the digital camera 1.

In the case of pixel for which no chromophore data is generated by the conversion module 12, this difference data will correspond to the RGB values for the corresponding pixels in the original image. Where the conversion module 12 is able to derive chromophore distribution data for a particular pixel, if the derived RGB values for a particular pixel do not exactly correspond to the RGB values for that pixel in the original image, this indicates that some of the apparent colouring of the area of skin represented by that pixel arises due to factors other than the estimated concentrations of blood and melanin for that area of skin. The array of differences in RGB values is then output as texture data which is passed to the combination module 24.

In addition to processing the original chromophore distribution data output by the conversion module 12 and the radial spherical co-ordinate data output by the spherical conversion module 10, in this embodiment the image generation module 18 is also arranged to process (S3-6) the revised chromophore distribution data generated by the treatment simulation module 16 in a similar way to generate $\theta$ and $\psi$ values which together with the radial value r for individual pixels are indicative for a particular portion of skin of the appearance of that portion after treatment which results in the change in chromophore distribution determined by the treatment simulation modules 16.

As in the case of the processing of the original chromophore distribution data, this is achieved by the image generation module 18 accessing the inverse conversion table 20 to convert determined blood and melanin concentration values for individual pixels into $\theta$ and $\psi$ values. The obtained $\theta$ and $\psi$ values together with the original radial r element of the spherical co-ordinate determined for a pixel are then processed in a conventional way described above to convert the obtained $\theta$ $\psi$ r values into conventional RGB values for that pixel representing the intensities in the red, green and blue channels for the portion of the individual represented by that pixel. This processing is repeated for all the pixels for which a chromophore distribution has been determined by the conversion module 12. The generated array of red, green and blue pixel values is then output by the image generation module 18 as a treated image and passed to the combination module 24.

Figure 4E:
FIG. 4E is an image generated utilising the blood and melanin distributions illustrated in FIGS. 4D and C.

Thus by way of example in the case of the modified blood image of FIG. 4D, the melanin image of FIG. 4C and the radial co-ordinate values determined by processing the image of FIG. 4A, a treated image indicative of the appearance of the individual appearing in the image of FIG. 4A where the blood vessels responsible for the thread veins has been treated so as to result in a distribution of blood as shown in FIG. 4D would be generated and is illustrated as FIG. 4E.

As can be seen the result of the processing is to generate an image similar to that of the original image but where the disfigurement arising due to the thread veins has been removed. This difference may most clearly be seen by comparing the image portion corresponding to the original image portion highlighted in FIG. 5A a corresponding highlighted image portion from FIG. 4E which is shown in FIG. 5D.

As stated above since the conversion of angular spherical co-ordinates to a chromophore distribution and a reconversion of that a chromophore distribution to angular co-ordinates is based on the assumption that all of the variation in hue of a particular image portion rises due to variations in concentration of chromophore, the treated image generated by the image generation module 18 will lack features which arise due to other factors.

Figure 5A:
FIG. 5A is an enlarged portion of the image of the cheek of the individual appearing in FIG. 4A illustrating thread veins appearing in that image.
Figure 5B:
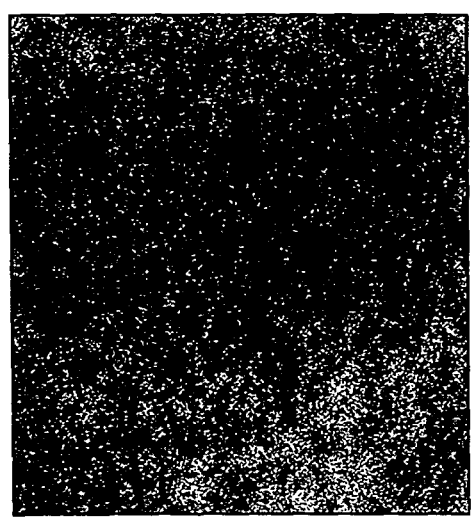
FIG. 5B is an illustration of the distribution of blood determined for the enlarged image portion of FIG. 5A.
Figure 5C:
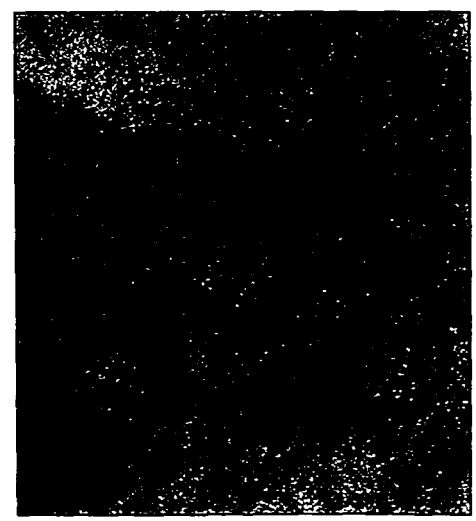
FIG. 5C is an illustration of a corrected distribution of blood illustrative of the expected distribution of blood after the treatment of the thread veins appearing in FIG. 5A.
Figure 5D:
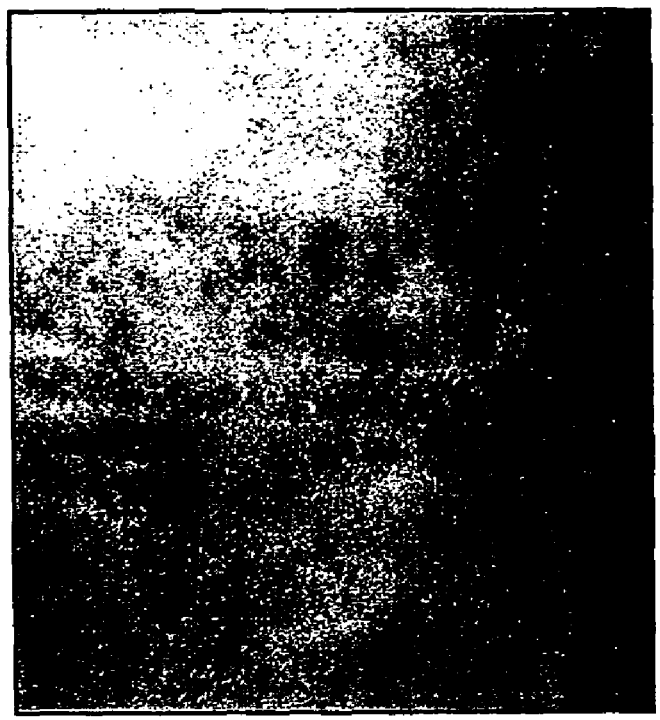
FIG. 5D is an enlarged portion of the image of FIG. 4E corresponding to the enlarged area of FIG. 4A shown in FIG. 5A.

Thus for example comparing FIG. 4A and FIG. 4E and also FIGS. 5A and 5D, the generated images of FIGS. 4E and 5D appear to lack texture when compared with the corresponding original images of FIGS. 4A and 5A. This can be seen most clearly in the portion of the images corresponding to the individual's eye appearing in the image.

Figure 6A:
FIG. 6A is an enlarged portion illustrating the eye of the individual in FIG. 4A.
Figure 6B:
FIG. 6B is an enlarged image portion illustrating the eye of the individual in FIG. 4E.

To illustrate these differences, the portion in the original image of FIG. 4A corresponding to the individual's eye is shown in FIG. 6A and the corresponding portion from the generated image of FIG. 4E is shown as FIG. 6B. As can be seen most clearly in these two images around the eye portion as a result of the processing much of the detailed texture of lines about the eye is lost.

As the detail which is lost through the conversion and reconversion of spherical co-ordinates is independent of any underlying manipulation of the chromophore distributions used to generate a treated image, this missing texture information in this embodiment is exactly the texture data for an image determined by the texture determination module 22.

Thus in this embodiment this missing information can therefore be reintroduced to the image by the combination module 24 varying the red, green and blue values for each pixel in the treated image by the corresponding red, green and blue values determined for those pixels determined by the texture determination module 22. In this embodiment this processing, in addition to reintroducing the missing texture, also causes pixels which the image conversion module 12 is unable to convert $\theta$ and $\psi$ spherical co-ordinates into chromophore concentrations to be represented by the original pixel values for those pixel from the original image obtained by the digital camera 1.

Figure 4F:
FIG. 4F is a final image derived by processing the image of FIG. 4E to add additional variations in appearance due to factors other than chromophore distributions of FIGS. 4C and 4D.
Figure 5E:
FIG. 5E is an enlarged portion of the image of FIG. 4F corresponding to the enlarged area of FIG. 4A shown in FIG. 5A.

A final image generated after reintroducing this texture to the treated image of FIG. 4E is shown in FIG. 4F. Highlighted portions of the final images corresponding to the portions shown in FIG. 5D and FIG. 6B are also illustrated as FIGS. 5E and 6C respectively.

Figure 6C:
FIG. 6C is an enlarged image portion of illustrating the eye of the individual in FIG. 4F.

As can be seen in particular in FIG. 6C, the addition of the texture data derived by the texture determination module reintroduces to the image the detailed texture which is missing from the generated image of FIG. 6B when compared with the original image of FIG. 6A.

The original image 33 generated by the camera and the final generated image 34 can then be output and displayed simultaneously as an output image 30 on a display 31 thereby illustrating to the individual the expected result of the treatment.

Second Embodiment

A second embodiment of the present invention will now be described with reference to FIGS. 7 and 8 which are a schematic block diagram of an image processing system in accordance with a second embodiment of the present invention and a flow diagram of the processing performed by the image processing system respectively.

In the first embodiment an image processing system was described in which an image generation module 18 generated a derived and treated image utilising chromophore distribution data and r co-ordinate data derived by a spherical conversion module 10. The derived image data was then processed by a texture determination module 22 to obtain texture data which was then combined with the generated treated image data by a combination module 24 in order to generate an output image.

In this embodiment and alternative image processing system will be described which generates output image data directly from derived and treated image data without utilising the r co-ordinates determined for an image by a spherical conversion module 10.

Referring to FIG. 7, the image processing system in accordance with this embodiment of the present invention is identical to the image processing system of the previous embodiment with the exception that the texture determination and combination modules 22, 24 are replaced by an output module 100 and the image generation module 18 and the inverse conversion table 20 are replaced with a modified image generation module 101 and a modified inverse conversion table 102. The remaining elements of the system and are identical to the elements previously described in relation to the first embodiment and are identified by the same reference numerals as were previously used in FIG. 1.

Figure 8:
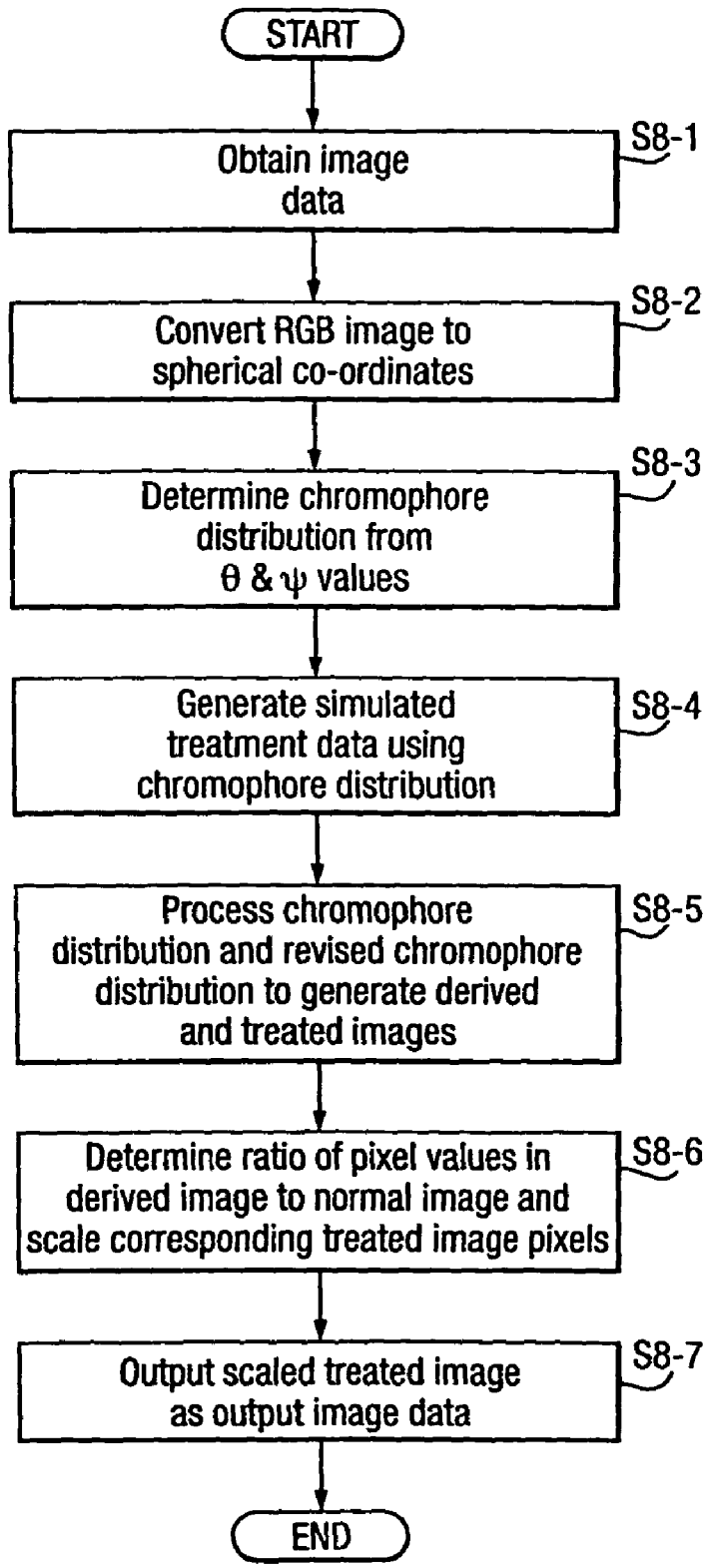
FIG. 8 is a flow diagram of the processing performed by the image processing system of FIG. 7.

The processing performed by the image processing system of FIG. 7 is illustrated by the flow diagram of FIG. 8. The processing by the system to derive chromophore distribution data from input image data and to derive simulated treatment data using that chromophore distribution data (s8-1-s8-4) is identical to the corresponding steps (s3-1-s3-4) undertaken in the first embodiment and description of these steps will not be repeated.

After the image processing system in FIG. 7 has derived chromophore distribution data and simulated treatment data, this data is then processed (s8-5) by the image generation module 101.

More specifically, in this embodiment the image generation module 101 processes the derived chromophore distribution data and simulated treatment data by accessing a modified inverse conversion table 102 which in this embodiment comprises a look up table associating pairs of blood and melanin concentrations with RGB values representative of the apparent colour of skin having such blood and melanin concentrations as viewed under fixed lighting conditions.

The RGB values stored in the modified inverse conversion table 102 could be generated by storing empirical data of the appearance of skin containing specific blood and melanin concentrations as viewed under fixed lighting conditions. However, in this embodiment, the RGB values comprise calculated RGB values determined by applying the inverse function relating blood and melanin concentrations to $\theta$ and $\psi$ spherical co-ordinates as defined by data in the conversion table 14 and converting the determined $\theta$ and $\psi$ spherical co-ordinates to RGB values using a fixed value for r.

As in the previous embodiment, the image generation module 101 processes each pair of chromophore concentration values in the chromophore distribution and the revised chromophore distribution in turn. As a result of the processing of the arrays defining the chromophore distributions performed by the image generation module 101, the image generation module 101 generates a pair of RGB images. These images are then passed to the output module 100.

As has previously been stated when RGB image data is converted to spherical co-ordinate data the angular $\theta$ $\psi$ co-ordinates are substantially indicative of the hue and chromaticity represented by an individual pixel which arises due to the presence and concentrations of chromophores such as blood and melanin in the skin. The radial co-ordinate r is then substantially indicative of the brightness of the pixel which arises due to a combination of lighting factors and the concentrations of collagen in the skin. As in this embodiment, the RGB values for pixels in the derived and treated images are generated utilising a constant r value, the images will be representative of areas of skin under fixed lighting conditions and where the concentration of collagen is constant.

In order to generate an image representative of an individual under true lighting conditions and representative of varying amounts of collagen, output RGB data for each pixel in an image is derived (s8-6) utilising the following equations:

$$R_{out}(x, y) = \frac{R_{original}(x, y)}{R_{derived}(x, y)} R_{treated}(x, y)$$

-continued $$G_{out}(x, y) = \frac{G_{original}(x, y)}{G_{derived}(x, y)} G_{treated}(x, y)$$

$$B_{out}(x, y) = \frac{B_{original}(x, y)}{B_{derived}(x, y)} B_{treated}(x, y)$$

where $R_{out}(x,y)$, $G_{out}(x,y)$ and $B_{out}(x,y)$ are the output RGB values for a pixel at position x,y and $R_{original}(x,y)$, $R_{derived}(x,y)$ $R_{treated}(x,y)$, $G_{original}(x,y)$, $G_{derived}(x,y)$ $G_{treated}(x,y)$, $B_{original}(x,y)$, $B_{derived}(x,y)$ $B_{treated}(x,y)$ are the red green and blue values for corresponding pixels at position x,y in an original image obtained by the digital camera 1 and in the derived and treated images generated by the image generation module 101 respectively.

By determining for each colour channel in each pixel the ratio of a colour value in the original image output by the camera 1 to the corresponding colour value in a generated derived image and then scaling the corresponding colour value in a treated image by that ratio, a means is provided to vary the brightness of each pixel so as to reflect the variations in apparent brightness due to variations in lighting and collagen concentration present in the original image and thereby generate a realistic final output image. Finally, a generated output image is output (s8-7) and displayed on a display screen 31.

Third Embodiment

A third embodiment of the present invention will now be briefly described with reference to FIGS. 9A and B.

In the first and second embodiments a system for generating images simulating the effect of the treatment for thread veins has been described, it will be appreciated that the described system could be modified to simulate any cosmetic or surgical treatment which varies the distribution of choromophores within the skin of an individual. Thus for example in other embodiments, images generated on the basis of a revised melanin distribution might be created. Such a system could for example simulate the effect of an acid peel on the appearance of age spots.

Alternatively the present invention could be utilised to illustrate the effect of the progression of an aliment or of aging. In such an embodiment, the treatment simulation module 16 of the first and second embodiments would be modified so as to process obtained chromophore distributions generated by the image conversion module 12 to generate a revised chromophore distribution where the revised chromophore distribution was representative of a distribution arising due to an aliment or through aging.

Figure 9A:
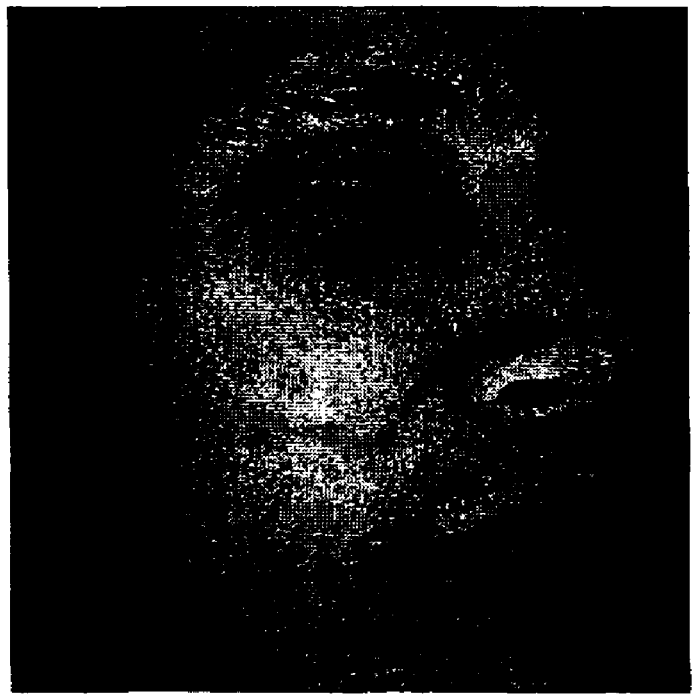
FIGS. 9A and 9B are a pair of illustrative images generated by a third embodiment of the present invention.
Figure 9B:
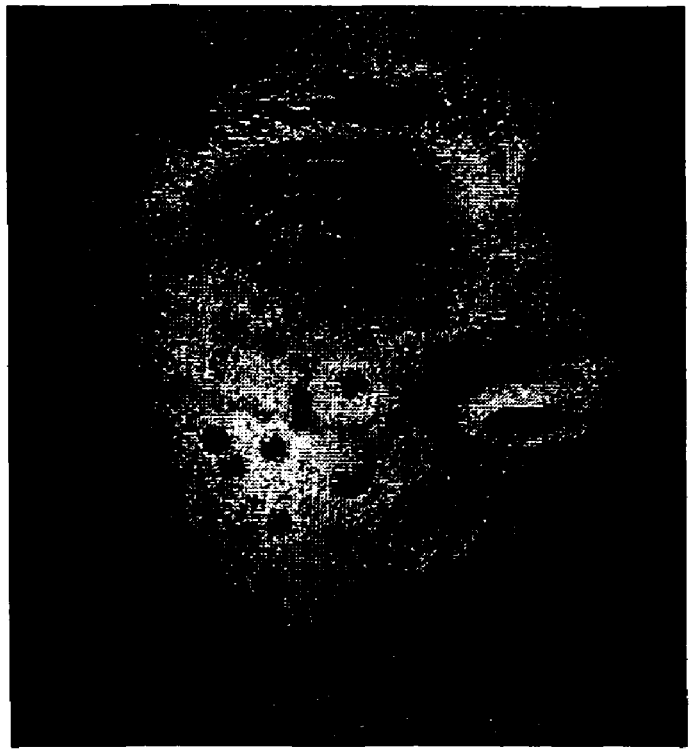

Thus for example referring to FIGS. 9A and B, FIG. 9A is an illustrative example of an original image of an individual. FIG. 9B is an illustrative example image generated by a third embodiment of the present invention in which the appearance of acne on the face of the individual is simulated by processing a determined chromophore distribution for the image of FIG. 9A.

Other alternative embodiments could for example generate modified chromophore distributions and generate representations of other conditions and ailments such as for example sunburn.

Alternative Embodiments and Modifications

In the first above described embodiment, a system has been described in which an image illuminated by polarised light is obtained. By obtaining an image through a cross polarising filter 36, specular reflections directly from the surface of an individual's skin are eliminated.

It will be appreciated that in alternative embodiments, in addition to obtaining an image of an individual in which specular reflections have been eliminated, a further image could be obtained when the absence of the cross polarising filter 36. The image obtained in the absence of the cross polarising filter 36 could then be processed by the texture determination module 22 so as to generate texture data which identifies the difference between a derived image and an image obtained in the absence of the polarising filter 36. When this texture data is combined with a treated image, a final output image would then be generated where the output image included not only the texture missing from a derived image but also the difference in appearance resulting from specular reflections from the surface of the skin. The advantage of such a system would be that the images generated by the computer would be more realistic as the direct reflections would also be present in the generated images.

It will be appreciated that in a system where images are obtained both in the presence and the absence of a polarising filter 36, either two images could be obtained successively with the polarising filter 36 being removed or alternatively an additional digital camera could be provided solely for the purpose of obtaining image data in the absence of the cross polarising filter 36.

In the above embodiments, systems involving the manipulation of a single chromophore distribution have been described. It will be appreciated that in other embodiments, modified chromophore distributions for more than one chromophore might be generated and simulated images created based on the revised chromophore distributions for more than one chromophore could be created.

Although in the above described embodiments, a system has been described in which measurements of the concentration of blood and melanin are obtained, it will be appreciated that the system could be modified to obtain measurements of other chromophores such as bilirubin, tattoo pigments or dye stuffs, keratin and hair. In such alternative embodiments the wavelengths of emitted light detected by a digital camera could be selected so as to measure wavelengths which are substantially unaffected by the presence of for example melanin. Processing such measurements in the way described would enable measurements of other chromophores to be obtained.

Alternatively instead of obtaining only three measurements corresponding to the red, green and blue channels in an image obtained by a digital camera, a modified camera obtaining intensity measurements for more wavebands could be provided and the additional measurements could be utilised to determine measurements of for example blood, melanin and collagen concentrations. In such a system in addition to the usual red, green and blue channels a digital camera arranged to obtain measurements in an infrared region might be utilised.

In other embodiments means could be provided to process the chromophore distribution data generated by the image conversion module to identify abnormal distributions of chromophores. The processing performed by a treatment simulation module could then be selected to normalise the abnormal distributions.

Thus for example in the case of thread veins abnormally high concentrations of blood might be automatically detected and replaced with an average expected concentration for a particular body part. In other embodiments abnormally high or low concentrations of other chromophores might be detected and corrected.

Although in the above embodiments reference has been made to obtaining measurements of melanin concentrations, it will be appreciated that embodiments could be provided where measurements of the distribution and concentration of different types of melanin could be provided. Thus for example in some embodiments a system could be provided so that measurements of melanin comprised measurements of the distribution of only eumelanin or alternatively measurements of only pheomelanin rather than total melanin measurements.

Although in the above described embodiments generated image data has been described as being output as a screen image, it will be appreciated that if a 3D computer model of an individual appearing in an image is available the generated image data could be used as texture render data for texture rendering a model thereby generating a 3D model of an individual's appearance utilising a revised chromophore distribution.

Although the embodiments of the invention described with reference to the drawings comprise computer apparatus and processes performed in computer apparatus, the invention also extends to computer programs, particularly computer programs on or in a carrier, adapted for putting the invention into practice. The program may be in the form of source or object code or in any other form suitable for use in the implementation of the processes according to the invention. The carrier can be any entity or device capable of carrying the program.

For example, the carrier may comprise a storage medium, such as a ROM, for example a CD ROM or a semiconductor ROM, or a magnetic recording medium, for example a floppy disc or hard disk. Further, the carrier may be a transmissible carrier such as an electrical or optical signal which may be conveyed via electrical or optical cable or by radio or other means.

When a program is embodied in a signal which may be conveyed directly by a cable or other device or means, the carrier may be constituted by such cable or other device or means.

Alternatively, the carrier may be an integrated circuit in which the program is embedded, the integrated circuit being adapted for performing, or for use in the performance of, the relevant processes.

While the foregoing is directed to embodiments of the present invention, other and further embodiments of the invention may be devised without departing from the basic scope thereof.

What is claimed is:

1. An image processing apparatus comprising:
a data store operable to store model data defining a relationship between data indicative of an apparent colour of skin derived from image data and concentrations of one or more chromophores in the skin;
a distribution determination module operable to process received image data representative of an image of an individual and use the model data stored in said data store to determine a distribution of at least one chromophore in skin of the represented individual;
a treatment simulation module operable to process the determined distribution of at least one chromophore determined by said distribution determination module to generate data simulating a revised chromophore distribution resulting from treatment of the individual;
a variation determination module operable to determine ratios for scaling the revised chromophore distribution to produce an image, the ratios being ratios of colour values in the received image data to corresponding colour values in the distribution determined by said distribution module; and
an image data generation module operable to generate data representative of an individual by converting said revised chromophore distribution to colour values and scaling the colour values of said revised chromophore distribution by said ratios determined by the variation determination module, according to the following equation:

$$R_{out}(x,y) = \frac{R_{original}(x,y)}{R_{derived}(x,y)} R_{treated}(x,y)$$

$$G_{out}(x,y) = \frac{G_{original}(x,y)}{G_{derived}(x,y)} G_{treated}(x,y)$$

$$B_{out}(x,y) = \frac{B_{original}(x,y)}{B_{derived}(x,y)} B_{treated}(x,y)$$

where $R_{out}(x,y)$, $G_{out}(x,y)$ and $B_{out}(x,y)$ are output red, green, and blue values for a pixel at position x,y and $R_{original}(x,y)$, $R_{derived}(x,y)$, $R_{treated}(x,y)$, $G_{original}(x,y)$, $G_{derived}(x,y)$, $G_{treated}(x,y)$, $B_{original}(x,y)$, $B_{derived}(x,y)$, $B_{treated}(x,y)$, are red, green and blue values for corresponding pixels at position x,y in the received image data received by the distribution determination module and in the determined and revised data generated by the distribution determination module and the treatment simulation module respectively.

2. The image processing apparatus of claim 1 further comprising: a camera operable to obtain image data representative of an individual; a light source operable to illuminate an individual with polarized light; and a polarizing filter operable to filter polarized light generated by said light source, wherein said camera is arranged to obtain image data representative of an individual illuminated by said light source via said polarizing filter.

3. The image processing apparatus of claim 2 wherein said camera is operable to obtain image data of an individual illuminated by said light source via said polarizing filter and image data representative of an individual illuminated by said light source in the absence of said polarizing filter, wherein said distribution determination module is operable to process image data of an individual illuminated by said light source obtained via said polarizing filter and said variation determination module is operable to utilise image data representative of an individual illuminated by said light source obtained in the absence of said polarizing filter to determine variations in appearance of an individual's skin due to factors other than the distribution of said at least one chromophore in the skin of the represented individual.

4. The image processing apparatus of claim 2 further comprising a camera operable to obtain image data representative of an individual in the absence of said polarizing filter wherein said distribution determination module is operable to process image data of an individual illuminated by said light source obtained via said polarizing filter and said variation determination module is operable to utilise image data representative of an individual illuminated by said light source obtained in the absence of said polarizing filter to determine variations in appearance of an individual's skin due to factors other than the distribution of said at least one chromophore in the skin of the represented individual.

5. The image processing apparatus of claim 1 wherein said processing module is operable to process a determined distribution of at least one chromophore to generate data representative of a revised chromophore distribution by identifying abnormal chromophore distributions and processing said identified abnormal chromophore distributions to reduce the detected abnormal distributions.

6. The image processing apparatus of claim 5 wherein said processing module is operable to process a determined distribution of at least one chromophore to generate data representative of a revised chromophore distribution by identifying excessive concentrations of one or more chromophores and processing said identified excessive chromophore concentrations to reduce the detected excessive concentrations.

7. The image processing apparatus with of claim 6 wherein said processing module is operable to process a determined distribution of at least one chromophore to generate data representative of a revised chromophore distribution by identifying excessive concentrations of one or more chromophores and processing said identified excessive chromophore concentrations to reduce the detected excessive concentrations by performing a blurring function.

8. An image processing method comprising:
  storing model data defining a relationship between data indicative of an apparent colour of skin derived from image data and concentrations of one or more chromophores in the skin;
  processing received image data representative of an image of an individual utilising said stored model data to determine the distribution of at least one chromophore in skin of the represented individual;
  processing a determined distribution of at least one chromophore to generate simulated treatment data representative of a revised chromophore distribution resulting from treatment of the individual;
  determining ratios for scaling the revised chromophore distribution to produce an image, the ratios being ratios of colour values in the received image data to corresponding colour values in the determined chromophore distribution; and
  generating image data representative of an individual by converting said revised chromophore distribution to colour values and scaling the colour values of said revised chromophore distribution by said ratios, according to the following equation:

$$R_{out}(x, y) = \frac{R_{original}(x, y)}{R_{derived}(x, y)} R_{treated}(x, y)$$

$$G_{out}(x, y) = \frac{G_{original}(x, y)}{G_{derived}(x, y)} G_{treated}(x, y)$$

$$B_{out}(x, y) = \frac{B_{original}(x, y)}{B_{derived}(x, y)} B_{treated}(x, y)$$

where $R_{out}(x,y)$, $G_{out}(x,y)$ and $B_{out}(x,y)$ are output red, green, and blue values for a pixel at position x,y and $R_{original}(x,y)$, $R_{derived}(x,y)$, $R_{treated}(x,y)$, $G_{original}(x,y)$, $G_{derived}(x,y)$, $G_{treated}(x,y)$, $B_{original}(x,y)$, $B_{derived}(x,y)$, $B_{treated}(x,y)$, are red, green and blue values for corresponding pixels at position x,y in the received image data received by the distribution determination module and in the determined and revised data generated by the distribution determination module and the treatment simulation module respectively.

9. The image processing method of claim 8, further comprising: illuminating an individual with polarized light from a light source operable to generated polarized light; and obtaining image data representative of said individual illuminated with polarized light as viewed via a polarizing filter operable to filter light having the same polarization as light generated by said light source.

10. The image processing method of claim 9 further comprising obtaining image data representative of said individual illuminated with polarized light in the absence of said polarizing filter, wherein processing received image data to determine the distribution of at least one chromophore in the skin comprises processing image data representative of an individual illuminated with polarized light as viewed via a polarizing filter operable to filter light having the same polarization as light generated by said light source and wherein determining variations in the appearance of an individual's skin due to factors other than the distribution of said at least one chromophore comprises utilising the determined distribution of at least one chromophore and received image data representative of an image of an individual illuminated with polarized light obtained in the absence of said polarizing filter.

11. The image processing method of claim 8 wherein processing a determined distribution of at least one chromophore to generate data representative of a revised chromophore distribution comprises identifying abnormal chromophore distributions and processing said identified abnormal chromophore distributions to reduce the detected abnormal distributions.

12. The image processing method of claim 11 wherein said processing a determined distribution of at least one chromophore to generate data representative of a revised chromophore distribution comprises identifying excessive concentrations of chromophores and processing said identified excessive chromophore concentrations to reduce the detected excessive concentrations.

13. The image processing method of claim 12 wherein processing a determined distribution of at least one chromophore to generate data representative of a revised chromophore distribution comprises identifying excessive concentrations of chromophores and processing said identified excessive chromophore concentrations by performing a blurring function.

14. A recording medium storing computer interpretable instructions for causing a programmable computer to perform a method comprising:
  storing model data defining a relationship between data indicative of an apparent colour of skin derived from image data and concentrations of one or more chromophores in the skin;
  processing received image data representative of an image of an individual utilising said stored model data to determine the distribution of at least one chromophore in skin of the represented individual;
  processing a determined distribution of at least one chromophore to generate simulated treatment data representative of a revised chromophore distribution resulting from treatment of the individual;
  determining ratios for scaling the revised chromophore distribution to produce an image, the ratios being ratios of colour values in the received image data to corresponding colour values in the determined chromophore distribution; and
  generating image data representative of an individual by converting said revised chromophore distribution to colour values and scaling the colour values of said revised chromophore distribution by said ratios, according to the following equation:

$$R_{out}(x, y) = \frac{R_{original}(x, y)}{R_{derived}(x, y)} R_{treated}(x, y)$$

$$G_{out}(x, y) = \frac{G_{original}(x, y)}{G_{derived}(x, y)} G_{treated}(x, y)$$

$$B_{out}(x, y) = \frac{B_{original}(x, y)}{B_{derived}(x, y)} B_{treated}(x, y)$$

where $R_{out}(x,y)$, $G_{out}(x,y)$ and $B_{out}(x,y)$ are output red, green, and blue values for a pixel at position x,y and $R_{original}(x,y)$, $R_{derived}(x,y)$, $R_{treated}(x,y)$, $G_{original}(x,y)$, $G_{derived}(x,y)$, $G_{treated}(x,y)$, $B_{original}(x,y)$, $B_{derived}(x,y)$, $B_{treated}(x,y)$, are red, green and blue values for corresponding pixels at position x,y in the received image data received by the distribution determination module and in the determined and revised data generated by the distribution determination module and the treatment simulation module respectively.

15. A recording medium in accordance with claim 14 comprising a computer disc.

16. A computer disc in accordance with claim 15 comprising a magnetic, optical or magneto-optical disc.

17. A recording medium in accordance with claim 15 comprising a signal in a communications network.

18. The image processing apparatus of claim 1 wherein said distribution determination module is operable to process received image data representative of an image of an individual to determine the distribution of at least one chromophore in the skin of the represented individual wherein said at least one chromophore comprises at least one chromophore selected from the list of blood, melanin, collagen, bilirubin, tattoo pigments or dye stuffs, keratin and hair.

19. The image processing apparatus in accordance with of claim 18 wherein said distribution determination module is operable to process received image data representative of an image of an individual to determine the distribution of blood and melanin in the skin of the represented individual.

20. The image processing method of claim 8 wherein said at least one chromophore comprises at least one chromophore selected from the list of blood, melanin, collagen, bilirubin, tattoo pigments or dye stuffs, keratin and hair.

21. The image processing method of claim 20 wherein processing received image data to determine the distribution of at least one chromophore in the skin of the represented individual comprises processing received image data to determine the distribution of blood and melanin in the skin of the represented individual.

22. The image processing apparatus of claim 1, wherein the distribution determination module processes received image data by converting colour values in the received image data from red, green, and blue colour values to angular spherical coordinates representing chromaticity of each pixel of the received image data to remove variations in appearance of the skin due to factors other than the concentration of at least one chromophore in the skin of the individual.

23. The image processing apparatus of claim 22, wherein the angular spherical coordinates are used to retrieve the model data stored in the data store to determine the distribution of at least one chromophore in the skin of the represented individual.

\* \* \* \* \*